(12) United States Patent
Veis

(10) Patent No.: US 11,517,403 B2
(45) Date of Patent: *Dec. 6, 2022

(54) ADJUSTABLE SLEEP APNEA ORAL APPLIANCE

(71) Applicant: Odin Sleep, LLC, Chatsworth, CA (US)

(72) Inventor: Robin Veis, Chatsworth, CA (US)

(73) Assignee: ODIN SLEEP, LLC, Chatsworh, CA (US)

(*) Notice: Subject to any disclaimer, the term of this patent is extended or adjusted under 35 U.S.C. 154(b) by 184 days.

This patent is subject to a terminal disclaimer.

(21) Appl. No.: 17/093,600

(22) Filed: Nov. 9, 2020

(65) Prior Publication Data

US 2021/0267720 A1    Sep. 2, 2021

Related U.S. Application Data

(63) Continuation of application No. 15/536,341, filed as application No. PCT/US2015/066209 on Dec. 16, 2015, now Pat. No. 10,828,131.

(60) Provisional application No. 62/092,761, filed on Dec. 16, 2014.

(51) Int. Cl.
*A61F 5/56* (2006.01)
*A61C 7/08* (2006.01)
*A61C 7/36* (2006.01)

(52) U.S. Cl.
CPC .......... *A61C 7/08* (2013.01); *A61C 7/36* (2013.01); *A61F 5/56* (2013.01); *A61F 5/566* (2013.01)

(58) Field of Classification Search
CPC ............ A61F 2005/563; A61F 5/566; A61F 2071/088; A61F 2071/086; A61F 71/085; A61F 5/56; A61F 5/58; A61C 7/08; A61C 7/36; A61B 5/4547; A61B 5/682

See application file for complete search history.

(56) References Cited

U.S. PATENT DOCUMENTS

| 4,541,800 A | * | 9/1985 | Bernstein | ............... A61C 7/00 433/6 |
| 5,499,633 A | * | 3/1996 | Fenton | ............... A61F 5/566 128/859 |
| 6,983,752 B2 | * | 1/2006 | Garabadian | ............ A61F 5/566 128/848 |
| 7,077,646 B2 | | 7/2006 | Hilliard | |
| 7,090,490 B2 | | 8/2006 | Graham et al. | |
| 7,637,262 B2 | | 12/2009 | Bailey | |
| 8,167,599 B2 | | 5/2012 | Harman et al. | |

(Continued)

FOREIGN PATENT DOCUMENTS

WO    2010/087824    8/2010

OTHER PUBLICATIONS

International Search Report and Written Opinion for PCT/US15/66209 dated Apr. 21, 2016; 6 pages.

(Continued)

*Primary Examiner* — Camtu T Nguyen
(74) *Attorney, Agent, or Firm* — Loza & Loza, LLP; Michael F. Fedrick

(57) ABSTRACT

An oral appliance having an upper tray, a lower tray, and axial inserts attached to either the upper tray or lower tray to adjust the relative position of a user's upper jaw and lower jaw in order to treat sleep apnea and/or snoring while at the same time allowing orthodontic treatment of the subject.

11 Claims, 13 Drawing Sheets

(56) References Cited

U.S. PATENT DOCUMENTS

| | | |
|---|---|---|
| 8,517,029 B2 | 8/2013 | Nelissen |
| 8,839,793 B2 | 9/2014 | Diaz |
| 9,820,882 B2 | 11/2017 | Liptak et al. |
| 2005/0199247 A1 | 9/2005 | Garabadian |
| 2009/0036889 A1 | 2/2009 | Callender |
| 2011/0005527 A1 | 1/2011 | Andrew et al. |
| 2012/0227750 A1 | 9/2012 | Tucker |
| 2012/0247485 A1 | 10/2012 | Timmons |
| 2013/0078594 A1 | 3/2013 | Leslie-Martin et al. |
| 2013/0089828 A1 | 4/2013 | Borovinskih |
| 2013/0269712 A1 | 10/2013 | Awde |
| 2013/0284184 A1 | 10/2013 | Wagner |
| 2014/0020691 A1 | 1/2014 | Sweeney et al. |
| 2014/0072927 A1 | 3/2014 | Diaz |
| 2014/0326252 A1 | 11/2014 | Quaka |
| 2015/0075540 A1 | 3/2015 | Dye |

OTHER PUBLICATIONS

International Preliminary Report on Patentability for PCT/US15/66209 dated Jun. 29, 2017; 5 pages.

Extended European Search Report for European Patent App. No. EP 15871025, dated Jun. 15, 2018.

\* cited by examiner

ADJUSTABLE SLEEP APNEA ORAL APPLIANCE

CROSS-REFERENCE TO RELATED APPLICATIONS

This application is a continuation of U.S. patent application Ser. No. 15/536,341, filed on Jun. 15, 2017, which was the U.S. national stage of International Patent Application No. PCT/US2015/066209, filed Dec. 16, 2015, which claims the benefit of priority under 35 U.S.C. § 119(e) from U.S. Patent Application No. 62/092,761, filed on Dec. 16, 2014 and titled ADJUSTABLE SLEEP APNEA ORAL APPLIANCE. The disclosures of the foregoing applications are incorporated herein by reference in their entirety.

BACKGROUND

Sleep apnea is a disorder characterized by abnormal pauses in breathing or instances of abnormally low breathing during sleep. Each pause in breathing, called an apnea, can last from a few seconds to minutes (typically lasting 20 to 40 seconds) and may occur 5 to 30 times or more an hour. Sleep apnea results from a partial-to-complete blockage of a subject's airway. Increased air speed through the airway causes an increase in dynamic pressure and a corresponding drop in static pressure. The decreased static pressure can in some instances draw back the lower jaw and tongue and thereby block the airway. This blockage can increase to the point of becoming complete, which at least temporarily interrupts breathing.

Subjects are generally at greater risk for sleep apnea if they are overweight or have conditions such as diabetes, hypertension, or chronic nasal congestion. There are a variety of factors, however, which can lead to sleep apnea. One factor is the presence of a narrow maxilla and/or mandible in a subject. Maxillary constriction may increase nasal resistance and alter the tongue posture, leading to narrowing of the retroglossal airway. Constriction of the maxilla and/or the mandible generally reduces intraoral air volume and tends to force the tongue back into the posterior airway space, leading to obstructive sleep apnea during sleep.

Orthodontics is a field of dentistry which focuses on the repositioning of a subject's teeth and jaws for aesthetic or other reasons, for example due to the "overcrowding" of a subject's teeth. Orthodontic methods typically require a subject to make continuous use of a dental appliance for a period of time in order to achieve results. The use of such appliances precludes the concurrent use of currently available oral appliances for treating sleep apnea. There remains a need therefore for improved devices and methods for treating sleep apnea in users of orthodontic appliances who experience sleep apnea.

SUMMARY

The present oral appliance comprises an upper tray and a lower tray which are respectively configured both to treat snoring and/or sleep apnea in a subject and to effect orthodontic treatment of the subject. In one embodiment, the upper tray comprises:
 (a) a receptacle bounded by the inner surface of the upper tray;
 (b) a right side upper bite pad connected at an upper end to the lower surface of the right side of the upper tray, wherein the bite pad comprises a lower surface, an anterior surface, a posterior surface, a right side, and a left side, the bite pad extending anteriorly from a posterior portion of the right side of the upper tray, wherein the lower surface of the bite pad is lower than the lower, coronal surface of an anterior portion of the right side upper tray;
 (c) a right side insert comprising an upper surface, a lower surface, an anterior surface, a posterior surface, a right side, and a left side, wherein the upper surface faces and/or contacts the lower surface of the right side of the upper tray anteriorly with respect to the right side upper bite pad, and wherein the posterior surface is configured to be reversibly attached to the anterior surface of the right side upper bite pad;
 (d) a left side upper bite pad connected at an upper end to the lower surface of the left side of the upper tray, wherein the bite pad comprises a lower surface, an anterior surface, a posterior surface, a right side, and a left side, the bite pad extending anteriorly from a posterior portion of the left side of the upper tray, wherein the lower surface of the bite pad is lower than the lower, coronal surface of an anterior portion of the left side upper tray;
 (e) a left side insert comprising an upper surface, a lower surface, an anterior surface, a posterior surface, a right side, and a left side, wherein the upper surface faces and/or contacts the lower surface of the left side of the upper tray anteriorly with respect to the left side upper bite pad, and wherein the posterior surface is configured to be reversibly attached to the anterior surface of the left side upper bite pad; and
 (f) a buccally facing anterior right side anchor on the outer buccal surface of the anterior portion of the right side of the upper tray, and a buccally facing anterior left side anchor on the outer buccal surface of the anterior portion of the left side of the upper tray.

In this embodiment, the lower tray comprises:
 (a) a receptacle bounded by the inner surface of the upper tray;
 (b) a right side lower bite pad connected at a lower end to the upper surface of the right side of the lower tray, wherein the bite pad comprises an upper surface, an anterior surface, a posterior surface, a right side, and a left side, the bite pad extending posteriorly from an anterior portion of the right side of the lower tray, wherein the upper surface of the bite pad is higher than the upper, coronal surface of a posterior portion of the right side lower tray;
 (c) a left side lower bite pad connected at a lower end to the upper surface of the left side of the upper tray, wherein the bite pad comprises an upper surface, an anterior surface, a posterior surface, a right side, and a left side, the bite pad extending posteriorly from an anterior portion of the left side of the lower tray, wherein the upper surface of the bite pad is higher than the upper, coronal surface of a posterior portion of the left side lower tray;
 (d) a buccally facing anterior right side anchor on the outer buccal surface of the anterior portion of the right side of the lower tray, and a buccally facing anterior left side anchor on the outer buccal surface of the anterior portion of the left side of the lower tray; and
 (e) a buccally facing posterior right side anchor on the outer buccal surface of the posterior portion of the right side of the lower tray, and a buccally facing posterior left side anchor on the outer buccal surface of the posterior portion of the left side of the lower tray, With the foregoing arrangement, the anterior surface of the right side insert forms an engagement surface which contacts the posterior surface of the right side lower bite pad, and the anterior surface of the left side insert forms an engagement surface which contacts the posterior surface of the left side lower bite pad. This limits the forward positioning of the upper tray with respect to the lower tray, thereby alleviating snoring and/or apnea when the oral appliance is used by a subject.

Another unique feature of the present appliance is that it allows orthodontic treatment of a subject while simultaneously treating snoring and/or apnea. In one embodiment, the receptacles of the upper tray and the lower tray are each configured to receive and retain orthodontic trays, preferably a series of orthodontic trays. In another embodiment, the receptacles of the upper tray and the lower tray are each configured to reposition one or more teeth of a subject and/or to change the configuration of a subject's mandible and/or maxilla when the appliance is worn by the subject.

In an alternative embodiment, the positions of the upper and lower bit pads can be reversed, so that the lower bite pad is positioned in a posterior portion of the lower tray, and the insert can be attached to the anterior end of the lower bite pad. In this case, the upper bite pad is positioned anteriorly, and the anterior surface of the insert engages the posterior surface of the upper bite pad.

FIGURES

DESCRIPTION

Definitions

Figure 1:
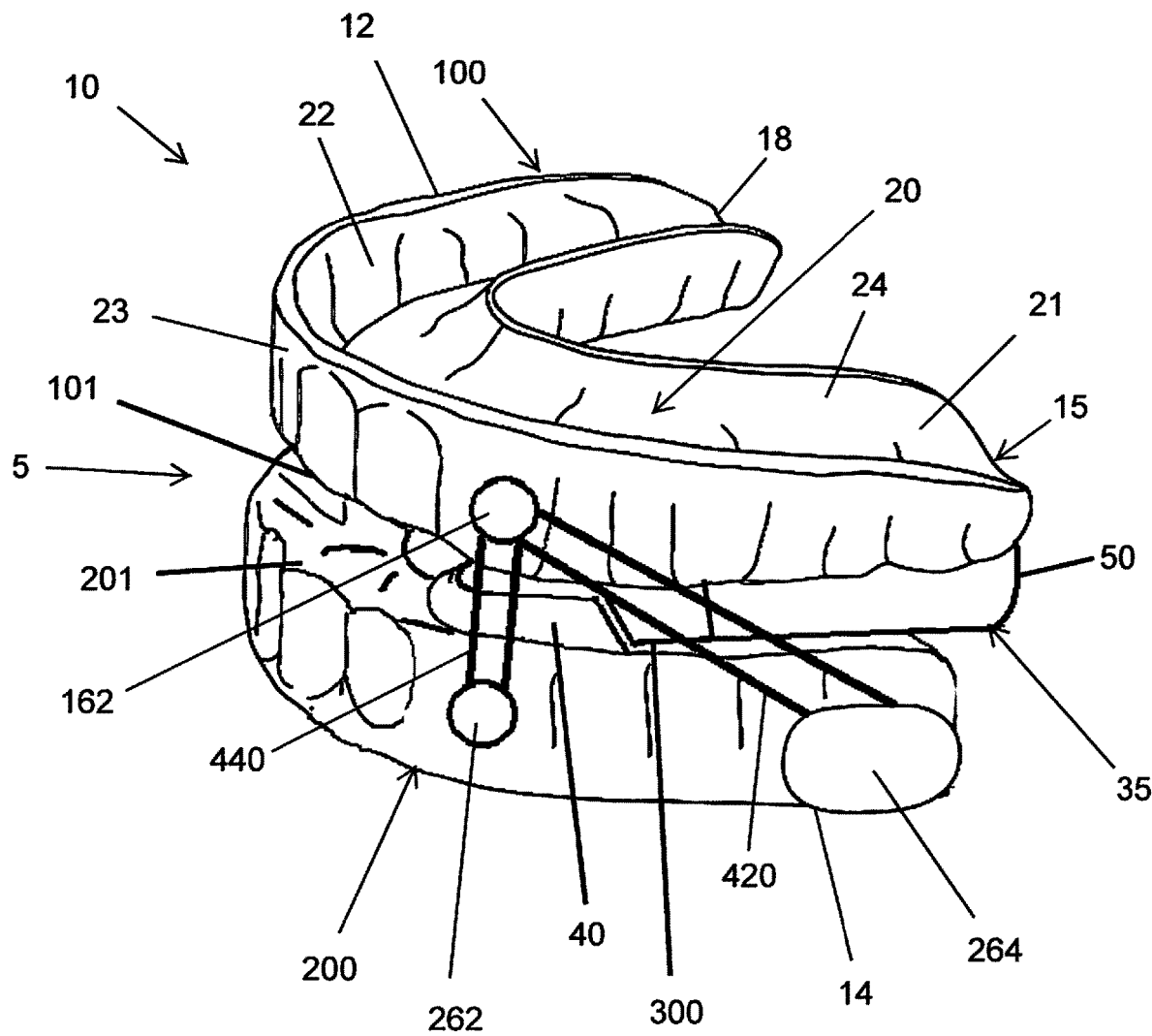
FIG. 1 is a left side, top perspective view of an embodiment of the present oral appliance, including elastic bands.
Figure 2:
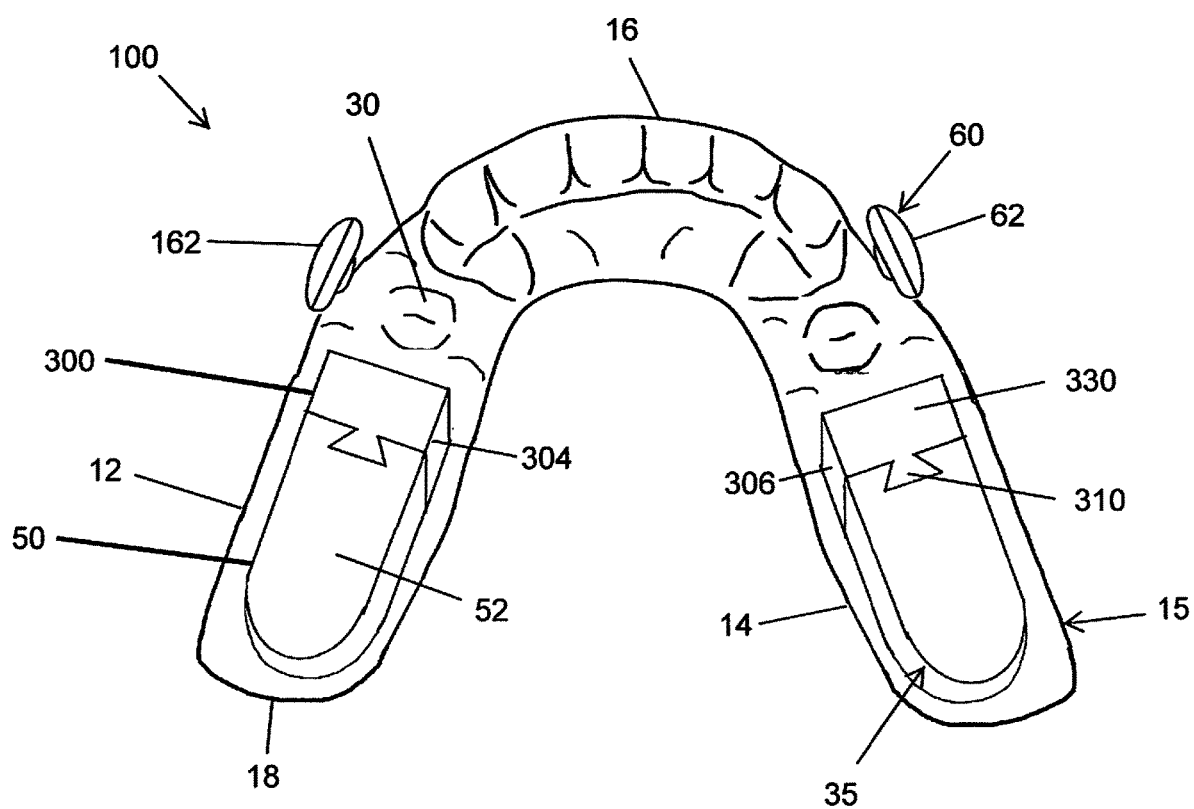
FIG. 2 is a top plan view of the upper portion of the appliance of FIG. 1.
Figure 3:
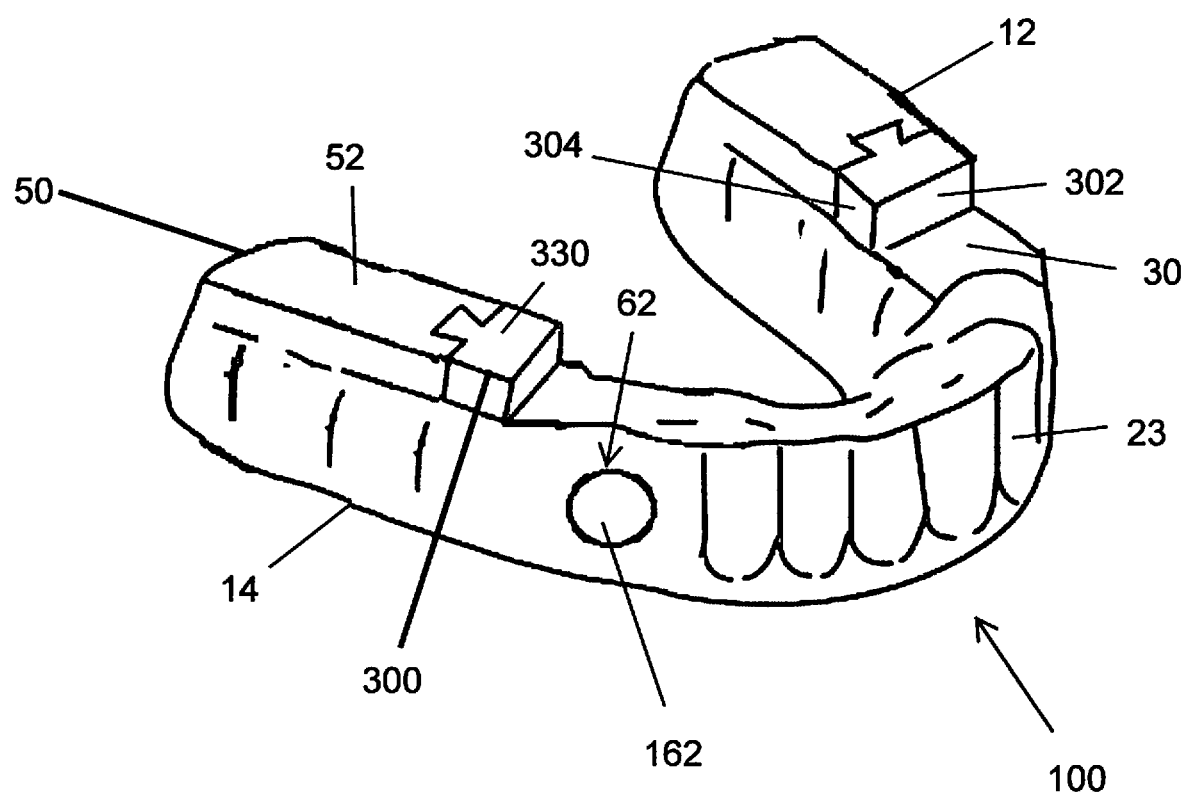
FIG. 3 is a left side, bottom perspective view of the upper portion of the appliance of FIG. 1.
Figure 4:
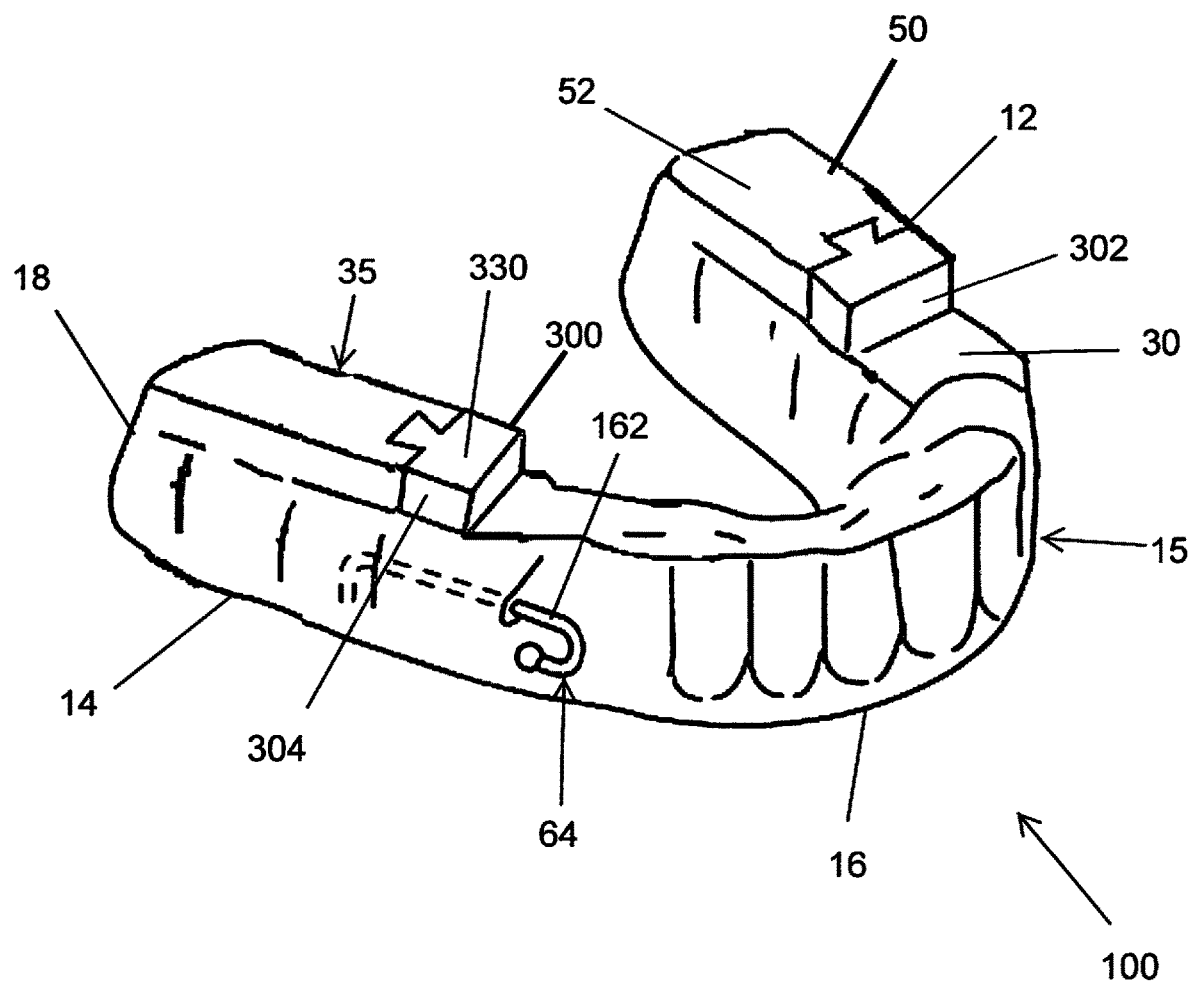
FIG. 4 is a left side, bottom perspective view of the upper portion of the appliance in another embodiment.

As used herein, the following terms and variations thereof have the meanings given below, unless a different meaning is clearly intended by the context in which such term is used.

"Anchor" refers to a component of the present appliance which is secured to a portion of the appliance and assists in connecting that portion to another portion of the appliance.

"Anterior" means in the direction of or toward or adjacent the front portion (opening) of a subject's mouth.

"Apnea" and "sleep apnea" refer to a temporary cessation of breathing and/or to instances of shallow or infrequent breathing during sleep, generally caused by a blockage of a subject's airway (referred to as obstructive sleep apnea).

"Buccal" means in the direction of or toward a subject's cheek. In relation to a subject's teeth, this refers to the side of the teeth facing the cheek.

"Coronal plane" refers to a hypothetical planar surface that extends through the body from the head to the feet, and divides the body into front and rear halves.

"Coronal" refers to a position or direction which is on or toward the distal end of a tooth (i.e., where the biting surface is located). A coronal surface is thus the biting surface of a tooth, which in posterior teeth is generally referred to as an occlusal surface and on anterior teeth is called an incisal surface. "Coronal surface" may also refer to the corresponding surface of a dental tray which contacts the other dental tray when the present device is worn by a user, i.e. to a lower surface of an upper dental tray or to an upper surface of a lower dental tray.

"Dental tray" refers to a structure comprising a receptacle for receiving the teeth of a subject. In some embodiments, the receptacle has an opening for receiving teeth and an interior surface which contacts the subject's teeth directly. In other embodiments, the receptacle receives an orthodontic tray.

"Downward" and "downwardly" mean in the direction of or toward a lower portion of a subject's body. "Upward" and "upwardly" mean in the opposite direction, i.e. in the direction of or toward an upper portion of a subject's body.

"Elongated" refers to a configuration or shape having a length which is longer than its width.

"Forward" means in a direction toward the anterior (front portion) of a subject's mouth.

"Horizontal," with respect to the present appliance, refers to disposition in a plane approximately perpendicular to the sagittal and/or the coronal plane of a subject, i.e. within 15 degrees of such a perpendicular plane.

"Labial" means in the direction of, toward, or adjacent to a subject's lips. In relation to a subject's teeth, this refers to the side of the front teeth facing the lips.

"Lateral" means away from the sagittal plane of a subject.

"Left" means to the left of the center sagittal plane of a subject, from the perspective of the subject.

"Lingual" means in the direction of, toward, or adjacent to a subject's tongue. In relation to a subject's teeth, this refers to the side of the teeth facing the tongue.

"Lower" refers to the relative position of a component in the present appliance which is closer to or toward a lower portion of a subject's body when being used. For example, and upper tray in the present appliance is positioned above (higher than) a lower tray when the appliance is worn by a user, i.e. such that the upper tray is fitted over the maxillary dentition and the lower tray is fitted over the mandibular dentition.

"Mandibular" refers to the lower jaw.

"Mandibular dentition" refers to the teeth of the lower jaw.

"Maxillary" refers to the upper jaw.

"Maxillary dentition" refers to the teeth of the upper jaw.

"Mechanically connected" means physically connected, either through a connection based on direct physical contact or via another mechanical structure.

"Medial" means toward the center sagittal plane of a subject.

"Orthodontic" refers to a feature or an appliance which repositions the teeth and/or jaw(s) of a subject.

"Orthodontic tray" refers to a dental tray for receiving the upper or lower dentition of a subject. An interior surface of an orthodontic tray contacts the subject's teeth directly with sockets or depressions sized to receive a subject's teeth.

"Post" refers to a component which protrudes from a surface and functions as a point of attachment for another component, such as an elastic band.

"Posterior" and "rearward" means in the direction of or toward or adjacent the rear portion of a subject's mouth.

"Right" means to the right of the center sagittal plane of a subject, from the perspective of the subject.

"Sagittal plane" refers to an imaginary plane that travels vertically from the top to the bottom of the body of a subject, dividing it into left and right portions.

"Subject" refers to a user of the present appliance, usually a human user.

"Thermoplastic" refers to a material, generally a polymer material, which may be softened by heat and hardened by cooling in a reversible physical process. The thermoplastic materials used in some components of the present appliance retain their shape at 100° F. and preferably become soft (deformable) at a temperature of 212° F. or below.

"Tray" and "dental tray," as used herein, refer to a generally U-shaped portion of the present appliance comprising an open area for receiving the maxillary or mandibular teeth of a subject, as the case may be.

"Upper" refers to the relative position of a component in the present appliance which is closer to or toward an upper portion of a subject's body when being used.

"Vertical," with respect to the present appliance, refers to disposition in a plane approximately parallel to the sagittal and/or the coronal plane of a subject, i.e. within 15 degrees of such a parallel plane. Preferably, vertical refers to a direction toward or away from a subject's head or feet.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise. With regard to relative terms, such as left and right, the term is to be interpreted from the perspective of a user of the present appliance when the appliance is being worn by the user, if no other orientation is indicated.

Oral Appliance

The present appliance 10 generally comprises a pair of dental trays 15, an upper tray 100 and a lower tray 200, which cooperate to position a subject's jaws so as to avoid sleep apnea. The upper tray 100 is fitted onto a subject's maxillary dentition, while the lower tray 200 is fitted to the subject's mandibular dentition. The tray portions 15 of the present device have an interior surface 21, an exterior surface 23, a right side 12, a left side 14, an anterior portion 16, and a posterior portion 18, and each comprise a generally U-shaped tooth-receiving receptacle 20 formed on one horizontal side of the tray 15 to fit over a subject's dentition.

In one embodiment, the receptacle 20 is configured to receive the teeth of a subject and to contact the teeth on an interior surface 21 of the tray 15. The receptacle 20 comprises lateral contiguous walls extending from a bottom surface facing the coronal surfaces of a subject's teeth toward the maxilla or mandible, respectively, i.e. buccal wall 22 and labial wall 24, so as to cover some or all of the buccal and labial sides of some or all of a subject's teeth. The trays 15 can be formed to conform to a subject's pre-existing dentition, or in a preferred embodiment can be formed to accomplish a change in the existing dentition and/or in the shape of a subject's mandible and/or maxilla, as described further below.

The exterior portions of the trays 15 comprise a coronal surface 30 formed on the horizontal side of the tray opposite the receptacle 20, i.e. on the exterior surface 23 of the tray 15. Each tray 15 further comprises a pair of respective bite pads 35 located on each lateral side of the tray 15, either a lower bite pad 40 or upper bite pad 50, which may be formed integrally with a respective tray 15 or may be bonded thereto. In the illustrated embodiments, the bite pads 35 separate the upper and lower jaws, to help treat apnea, and in addition provide an opening 5 between the upper incisal surface 101 and lower incisal surface 201 of the upper tray 100 and the lower tray 200, respectively, to allow air flow through a subject's mouth. Maintaining a subject's mouth in a slightly open position by separating the upper and lower jaws in this way also helps to treat apnea. In other embodiments, however, the upper incisal surface 101 and lower incisal surface 201 can contact each other.

In the illustrated embodiments, each lower bite pad 40 comprises a projection that extends distally with respect to the coronal surface 30 of the lower tray 200, i.e. upwardly when worn by subject wearing the present appliance 10. The lower bite pad 40 is located in an anterior portion 16 of each side 12, 14 of the lower tray 200, anterior to a lower occlusal surface 30 of the tray 200 in the illustrated embodiments, but in other embodiments (in which the upper bite pad 50 is located anteriorly) the lower bite pad 40 could be located in a relatively posterior position. The lower bite pad 40 comprises a generally horizontal coronal surface 42 for contacting a corresponding occlusal surface 30 in an anterior portion of the upper tray 100. Lower bite pad 40 further comprises a rearward-facing engagement surface 44 in the posterior portion of the bite pad 40 extending downwardly from the coronal surface 42 to the occlusal surface 30 of the exterior surface 23 of the lower tray 200.

The upper tray 100 likewise comprises a pair of upper bite pads 50, each of which extends downwardly from the exterior surface 23 of the upper tray 100. The upper bite pad 50 comprises a generally horizontal coronal surface 52 for contacting a corresponding occlusal surface 30 in a posterior portion of the lower tray 200, and a forward-facing connecting surface or connecting end 54 in the anterior portion of the upper bite pad 50. Each upper bite pad 50 comprises a projection that extends distally from the coronal surface 30 of the upper tray 100, i.e. downwardly when worn by subject wearing the present appliance 10, and includes a generally horizontal coronal surface 52 for contacting a corresponding occlusal surface in a posterior portion of the lower tray 200. The present appliance 10 is preferably configured such that when worn by a user, the coronal surface 52 of the upper bite pad 50 contacts the exterior, coronal surface 30 of the posterior portion of the lower tray 200 such that the coronal surface 42 of the lower bite pad 40 is simultaneously in contact with the coronal surface 30 of an anterior portion of the upper tray 100.

Figure 10:
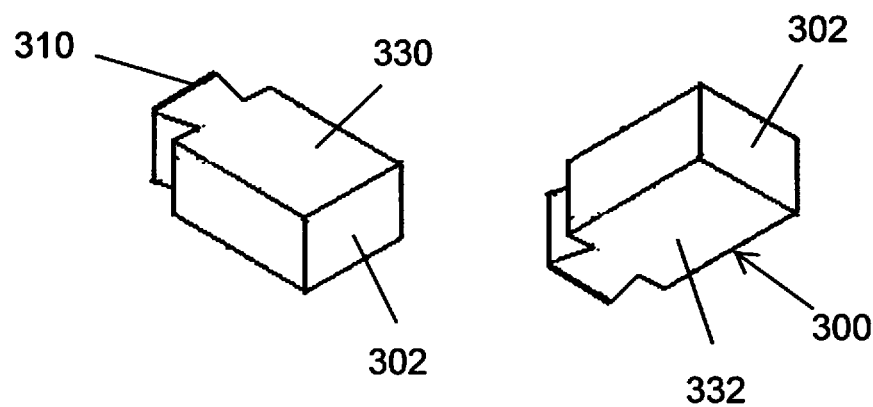
FIG. 10 is a front, top and front, bottom perspective view of an insert used with the present oral appliance.

A unique feature of the present oral appliance 10 is the use of axial inserts 300. The inserts 300 are configured to attach to one of the trays 15 and to engage a bite pad 35 on the other tray 15 of the present appliance 10. In the illustrated embodiments, the inserts 300 are attached to the upper tray 100 and engage the lower bite pad 40 of the lower tray. The bite pads 35 and inserts 300 together cooperate to limit and define the relative anterior-posterior positions of the maxilla and mandible of a user of the present appliance 10. As shown best in FIGS. 10-12, each insert 300 comprises an engagement surface 302, a right lateral side 304, a left lateral side 306, and an attachment end 310 opposite the engagement surface 302. The insert 300 further comprises a coronal surface (lower surface when attached to an upper tray 100) 330 and a tray contact surface (upper surface) 332 opposite the coronal surface 330. When the attachment end 310 of the insert 300 engages the connecting end 54 of the upper tray, the tray contact surface of the insert 300 abuts the occlusal surface 30 of the upper tray 100 and the coronal surface 330 of the insert 300 faces outwardly (downwardly). The coronal surface 330 is preferably parallel to the coronal surface 52 of the upper bite pad 50, and more preferably is configured in the same plane.

The attachment end 310 and the connecting end 54 are preferably provided with mutually fitting locking elements in order to retain the insert 300 on the upper tray 100. In the illustrated embodiments, the attachment end 310 of the insert 300 engages with the connecting end 54 of the upper tray 100 in a tongue-and-groove fashion, such that a laterally flaring wedge 312 fits within a recess 56 formed in the connecting end 54. As will be apparent to one of skill in the art, the insert 300 could alternatively be provided with a groove and the connecting end 54 could be configured with a forwardly projecting "tongue," or a differently configured projection could be used, such as a rounded sphere adapted to fit in a corresponding rounded hole. Other configurations can also be used to mechanically attach the insert 300 to the upper tray 100. In one alternative, an insert 300 could be attached to the upper bite pad 100 with an expansion screw, thereby allowing the length of the insert 300 to be further adjusted, as desired. It will also be apparent to those of skill in the art that the insert 300 could alternatively be attached to the lower tray 200, such as to the lower bite pad 40. In the illustrated embodiments, the sides 311, 313, and 315 of the wedge 312 preferably form an interference fit with the groove or recess 56 in order to securely retain the insert in the present appliance 10. In a preferred embodiment, the insert 300 and/or the upper bite pad 50 are formed from an elastomeric material, and the tongue of the attachment end 310 is formed with slightly larger dimensions than the recess 56, so that when the tongue is urged into the recess 56, it exerts an outward force that helps to retain it within the recess 56.

Once attached to the upper tray 100, the forward-facing engagement surface 302 of the insert 300 is positioned to contact the rearward-facing engagement surface 44 of the lower bite pad 40 when the present appliance 10 is worn by a user. As shown for example in FIG. 1, the insert's engagement surface 302 contacts the lower bite pad's engagement surface 44 so as to limit the rearward movement of the user's mandible with respect to the maxilla, and thereby assist in alleviating sleep apnea.

The insert engagement surface (anterior surface) 302 and lower bite pad engagement surface (posterior surface) 44 are preferably angled, opposed surfaces that interact to serve as advancement engagement surfaces for the mandible. Both the posterior face (engagement surface) 44 of the lower bite pad 40 and the anterior face (engagement surface) 302 of the insert may be angled, as shown in the illustrated embodiments, to assist in advancing the mandible as the trays 15 vertically close, employing a camming action. The engagement surface 44 is preferably disposed at a non-vertical angle with an upward and forward slant. The engagement surface 44 may employ an irregular, non-flat, arcuate, concave or convex surface or surface features that nonetheless allow the described sliding engagement. A vertical interface between the insert engagement surface 302 and lower bite pad engagement surface 44 is also possible.

Figure 8:
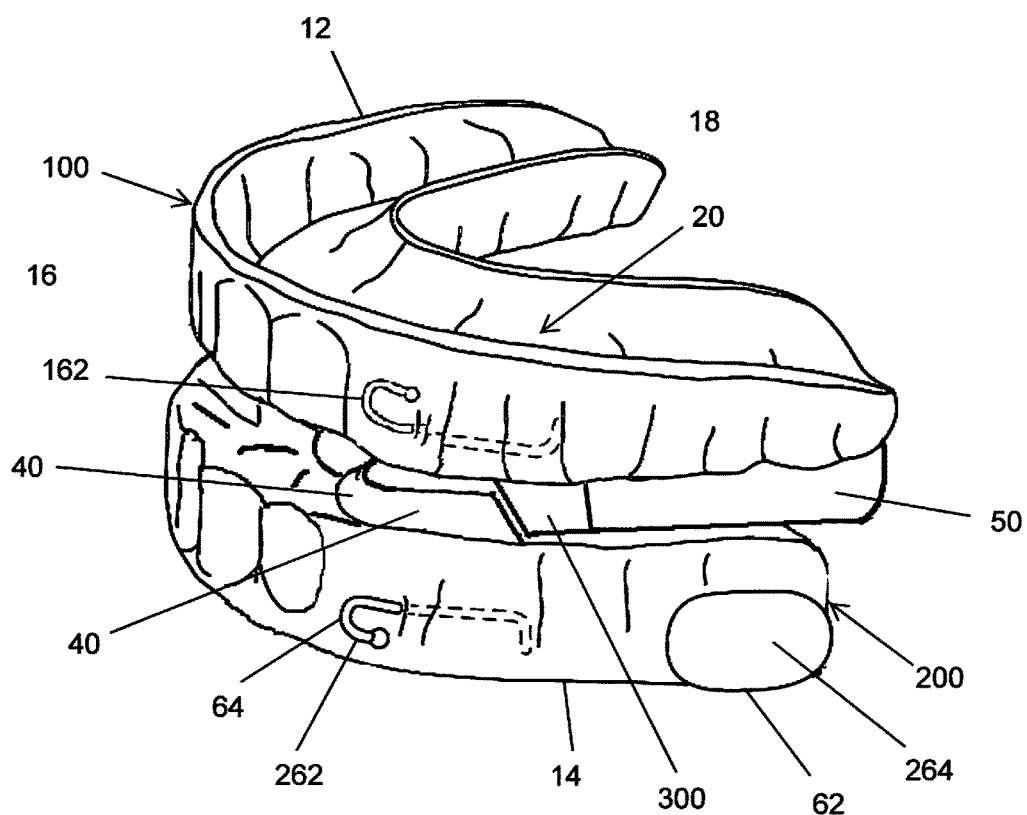
FIG. 8 is a left side, top perspective view of another embodiment of the present oral appliance.
Figure 11:
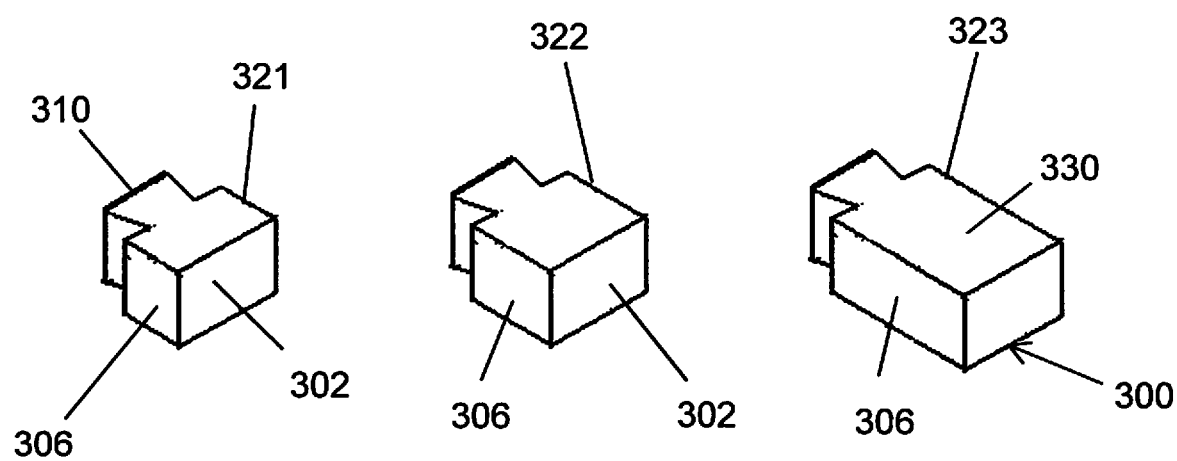
FIG. 11 is a front, top perspective view of three inserts used with the present oral appliance.
Figure 12:
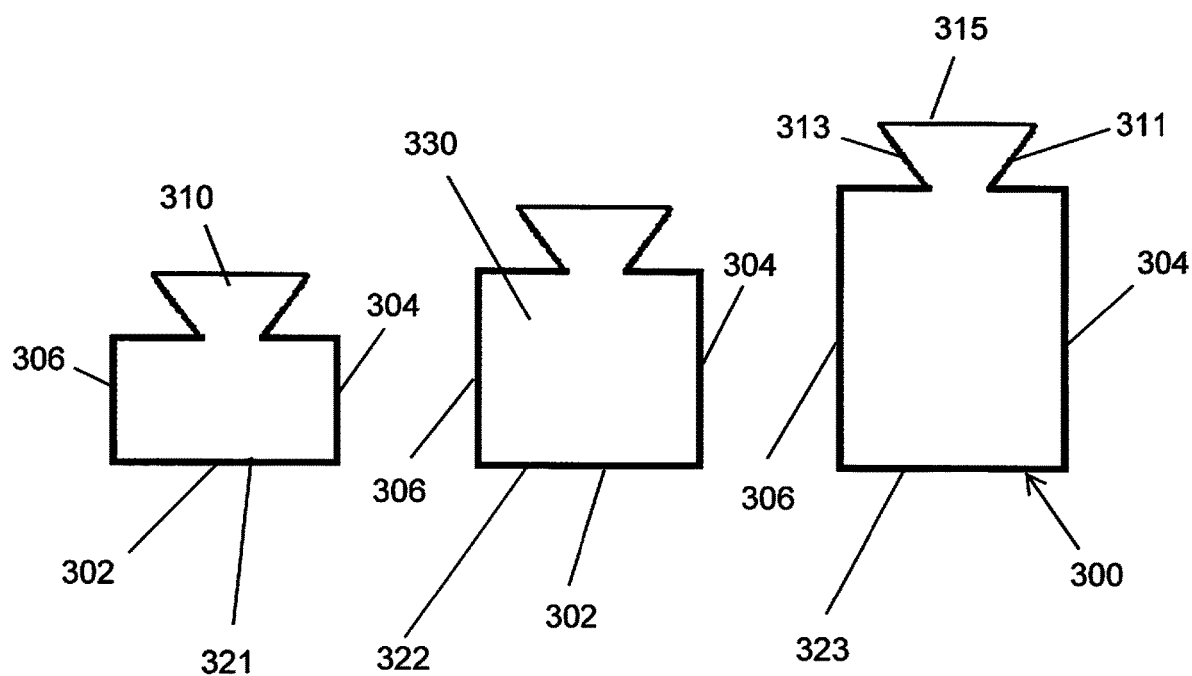
FIG. 12 is a top plan view of the inserts of FIG. 11.
Figure 13:
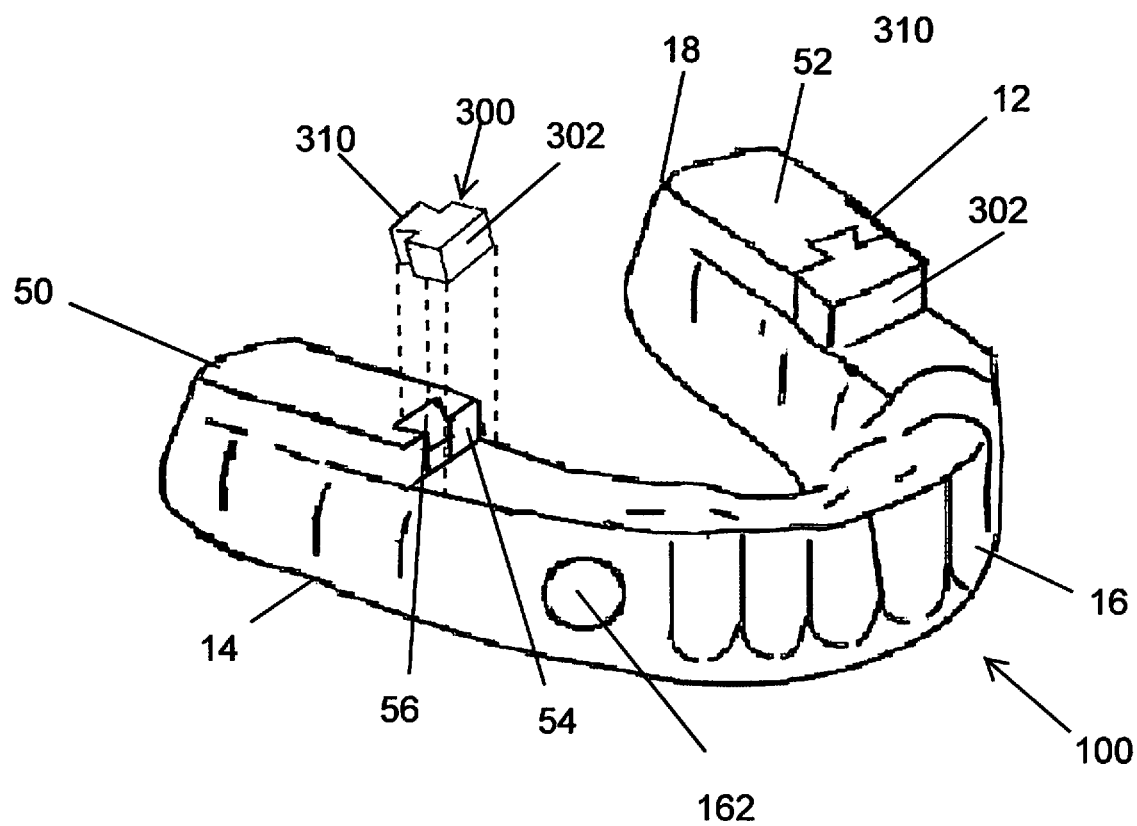
FIG. 13 is a left side, bottom perspective view of the upper portion of the appliance of FIG. 1, showing the placement of an insert.

In order to be able to adjust the relative position of a user's maxilla and mandible when the present appliance 10 is worn, inserts 300 of different lengths can be used. As shown in FIG. 8, the inserts 300 can be formed with lateral sides 304, 306 of different lengths, such that the engagement surfaces 302 of different inserts extend further forward or rearward, depending on the need of the user. In FIGS. 11 and 12, the inserts labeled 321, 322, and 323 comprise lateral sides 304, 306 of increasing length. As a result, a user's mandible can be positioned relatively anteriorly through the use of longer inserts, i.e. with longer lateral sides 304, 306, or can be positioned relatively posteriorly through the use of inserts with shorter sides. A set of inserts can be provided for use with the present appliance 10 having lateral sides that differ in increments of 1 mm, increments of 0.5 mm, or increments of 0.25 mm, for example. For this reason, attachment of the inserts 300 to the upper tray 100 via a mechanical connection is preferred, so that the attachment is reversible, and can be changed as needed. However, other means of engagement, such as through chemical means (e.g., glue) are also possible.

The upper and lower appliance trays 100, 200 are mechanically connected via anchors 60 in order to maintain the upper tray 100 in a predetermined position with respect to the lower tray 200. In particular, the anchor 162 of the left side portion of the upper tray 100 is mechanically connected to the anchor 262 of the left side portion of the lower tray 200, and the anchor 162 of the right side portion of the upper tray 100 is mechanically connected to the anchor 262 of the right side portion of the lower tray 200. The anchors can be, for example, a button 62, a hook 64, or a Herbst screw, and can be mechanically connected by appropriate connectors, such as orthodontic rubber bands, telescoping shims, and/or plastic connectors.

Figure 5:
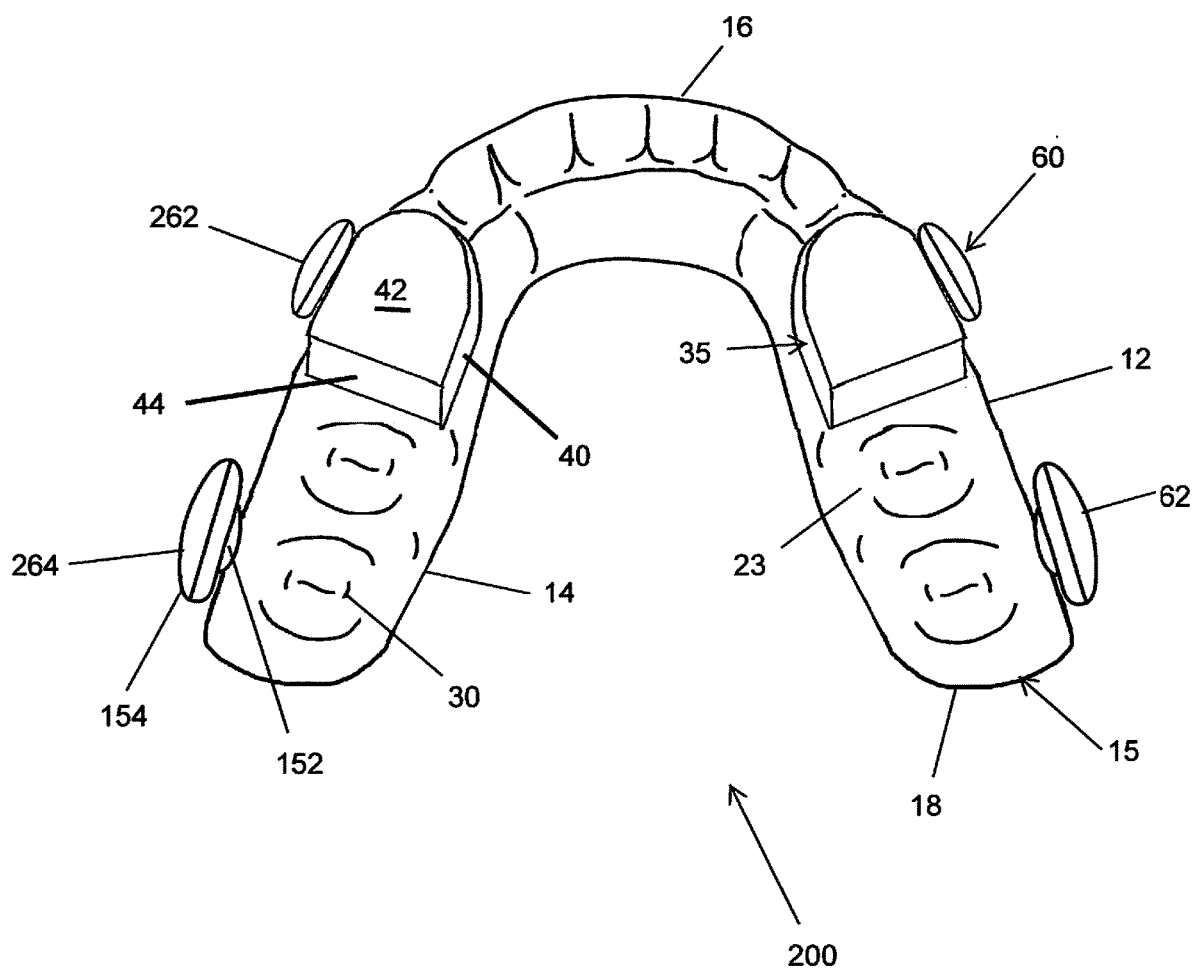
FIG. 5 is a top plan view of the lower portion of the appliance of FIG. 1.
Figure 6:
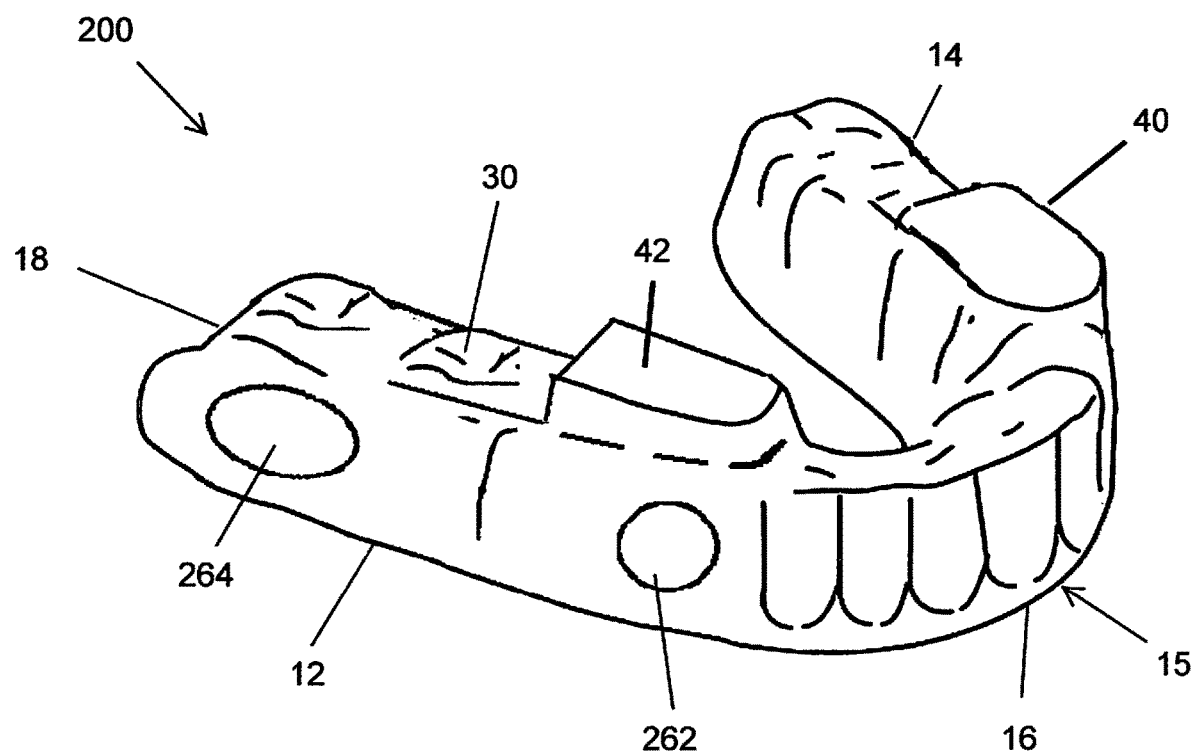
FIG. 6 is right side, top perspective view of the lower portion of the appliance of FIG. 1.
Figure 7:
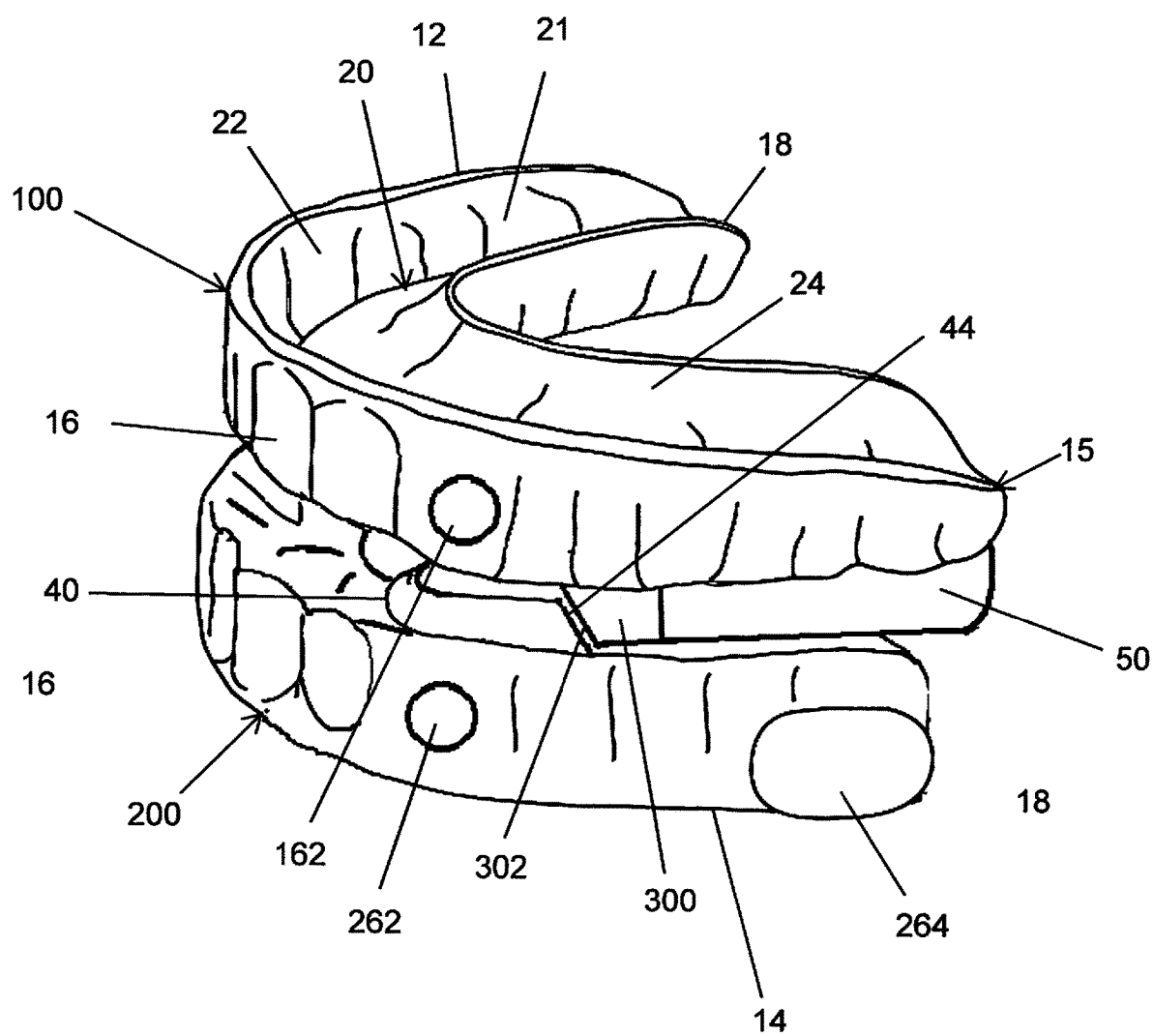
FIG. 7 is a left side, top perspective view of an embodiment of the oral appliance of FIG. 1.
Figure 9:
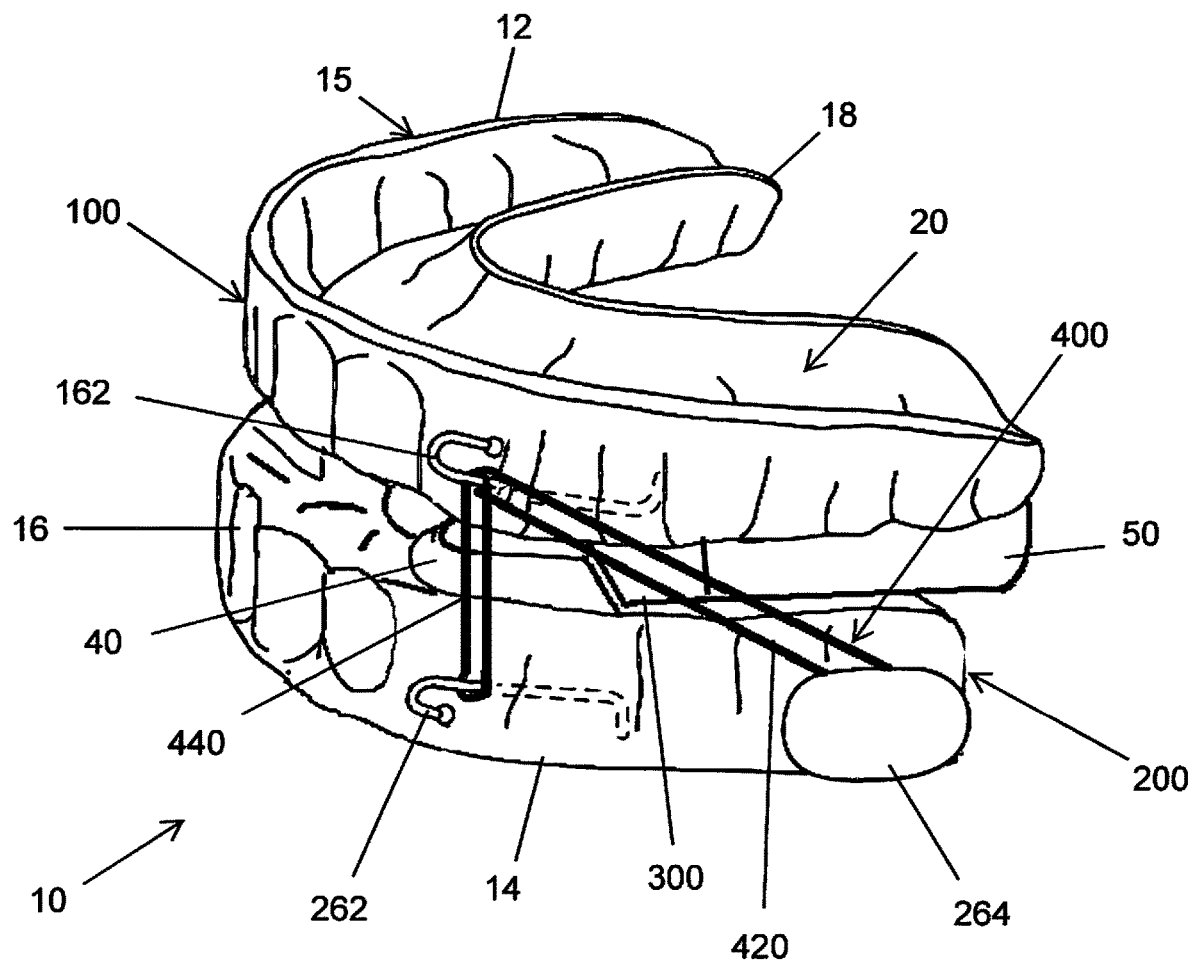
FIG. 9 is a left side, top perspective view of the embodiment of FIG. 8, including elastic bands.

As shown in the illustrated embodiments, once the trays 100, 200 have been fitted for a particular subject, elastic bands 400 are placed on buccal buttons 62 as shown in FIGS. 1 and 9. The buccal buttons 62 are posts or projections which extend buccally from the outer surfaces 23 of the upper tray 100 and lower tray 200, respectively. As seen in FIG. 5, they comprise a laterally extending portion 152 to which an elastic band 400 can be secured and a circumferential "button" portion 154 extending away from the axis of the laterally extending portion 152 at the distal end of the buccal button 62, in order to better secure an elastic band 400 on the buccal button 62.

In the illustrated embodiments, an anterior-posterior (diagonal) elastic band 420 extends from the anterior of the upper tray 100 to the posterior of the lower tray 200, between an upper anterior anchor 162 and a lower, relatively posterior anchor 264. The force exerted by this elastic urges the mandible forward in relation to the maxilla. A second, vertically extending elastic 440 extends between the upper anterior anchor 162 and a lower anterior anchor 262, generally between the first bicuspid region on both trays 50 and generally in vertical alignment. The vertically extending elastic 440 provides a "closed-mouth" posture during sleep. This combination of elastic bands gently holds the mandible in the position determined by the present appliance 10 and also encourages nasal breathing by preventing the mandible from opening and dropping back.

The present appliances 10 can be formed from a variety of orally compatible materials, typically polymers. In one embodiment, acrylic is used to form the present appliance. Thermoplastic polymers are typically used in the present appliance, but thermosets, thermoplastic elastomers, and other materials can also be used. The thermoplastic materials that are used must be capable of retaining their shape when used by a subject, and thus preferably remain solid at least at about 100° F., and preferably remain solid at somewhat higher temperatures, such as at 110° F., 120° F., or higher. When thermoplastic materials are used to form the present trays, they preferably become deformable at a temperature of 212° F. or less, so that they can be made plastic by being placed in boiling water. Preferably, the material is not deformable at less than 120° F., preferably at not less than 145° F.

Orthodontic Trays

In one embodiment, the trays 15 can be formed as a series of orthodontic dental trays for use by a subject. In this embodiment, trays 15 having differently-configured receptacle portions 20 are applied to the subject over time in order to reposition individual teeth in successive steps and/or to change the configuration of a subject's mandible and/or maxilla. The successive use of a number of such dental trays 15 permits each appliance to be configured to move individual teeth in small increments, typically less than 2 mm, preferably less than 1 mm, and more preferably less than 0.5 mm (referring to the maximum linear translation of any point on a tooth as a result of using a single appliance). The use of the inserts 300 of the present appliance 10 provides a great advantage when orthodontic trays are used in the present invention, because an optimum relative position of the mandible and maxilla of a user can be provided using an insert having a desired length, thereby addressing a user's sleep apnea while allowing orthodonture.

The tooth-receiving receptacle portions 20 of the dental trays 15 typically have a geometry corresponding to an intermediate or end tooth arrangement intended for a subject. When such a tray 15 is first worn by the subject, certain of the teeth will be misaligned relative to an undeformed geometry of the receptacle portion 20 of a tray 15. In this embodiment, the tray 15 is formed from a material that is sufficiently resilient to accommodate or conform to the misaligned teeth, but will apply sufficient resilient force against such misaligned teeth to reposition the teeth to the intermediate or end arrangement desired for that treatment step. The appliance will preferably, but not necessarily, fit over all teeth present in the upper or lower jaw. In some cases only certain teeth will be repositioned while will provide a base or anchor region for holding the repositioning appliance in place as it applies the resilient repositioning force against the tooth or teeth to be repositioned A subject's teeth are repositioned from an initial tooth arrangement to a final tooth arrangement by placing a series of incremental position adjustment appliances in the subject's mouth. The first tray appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the subject's mouth, where the final appliance has a geometry selected to progressively reposition teeth from the last intermediate arrangement to the final tooth arrangement.

In order to design a series of dental trays 15 that will reposition a particular subject's teeth, a digital data set representing an initial tooth arrangement and a final tooth arrangement can be determined. The initial data set representing the initial tooth arrangement, which can be presented as a visual image, is manipulated to reposition individual teeth. A final digital data set is then produced which represents the final tooth arrangement with repositioned teeth. The initial digital data set may be provided by conventional techniques, including digitizing X-ray images, images produced by computer-aided tomography (CAT scans), images produced by magnetic resonance imaging (MRI), and/or by other methods known to the art for producing three-dimensional digital representations of a subject's teeth. Alternatively, the initial digital data set may be provided by producing a plaster cast of the subject's teeth (prior to treatment) by conventional techniques, for example, and the plaster cast can then be scanned using laser or other scanning equipment to produce a high resolution digital representation of the plaster cast of the subject's teeth.

Once the initial and final data sets have been determined, a series of intermediate data sets, representing intermediate tooth positions for a subject's teeth, are determined. The successive intermediate digital data sets are preferably produced by determining positional differences between selected individual teeth in the initial data set and in the final data set and interpolating the differences. Such interpolation may be performed over at least three discrete stages, embodied in three different dental trays, more often at least ten, sometimes at least twenty-five, and occasionally forty or more. The interpolation can be a linear interpolation for some or all of the positional difference, or alternatively may be nonlinear. The positional differences will correspond to tooth movements where the maximum linear movement of any point on a tooth is preferably 2 mm or less, usually 1 mm or less, and preferably 0.5 mm or less.

Once the intermediate and final data sets have been determined, the appliances can be fabricated, such as with a rapid prototyping device or digital printer. Preferably, the appliance is polymeric and is formed from a thin sheet of a suitable elastomeric polymeric, such as Tru-Tain 0.03 in. thermal forming dental material (Tru-Tain Plastics, Rochester, Minn. 55902). One structure corresponding to each of the dental tray appliances is produced.

The foregoing dental tray appliances and their use in orthodontic treatment are described in U.S. Pat. No. 5,975,893 and in other patents assigned to Align Technology, Inc., including U.S. Pat. Nos. 621,562, 6,217,325, 6,398,548, 6,626,666, 6,629,840, 6,699,037, 7,134,874, 7,474,307, 8,105,080, and 8,562,340.

In embodiments in which tooth or jaw repositioning is not needed or desired, such as following a successful orthodontic treatment, the upper and lower dental trays 15 can be formed in ways known to the art. For example, when the present appliance is formed from a thermoplastic polymer, the upper dental tray 100 and lower dental tray 200 can be first evaluated for their fit with a subject's mouth, after which the trays can be softened, preferably by placing the appliance in near-boiling water for between several seconds and one minute. The softened appliance is then placed in the subject's mouth in alignment with the subject's upper and lower teeth, and the subject is instructed to bite into the softened material to make an impression of the teeth in the softened material. The tray material is then allowed to cool in the mouth for approximately one minute, after which the appliance is preferably soaked in cold water for an additional minute. Creating a customized dental impression in the trays of the present appliance in other ways and using other materials can be accomplished by one of skill in the art using known methods.

Figure 14:
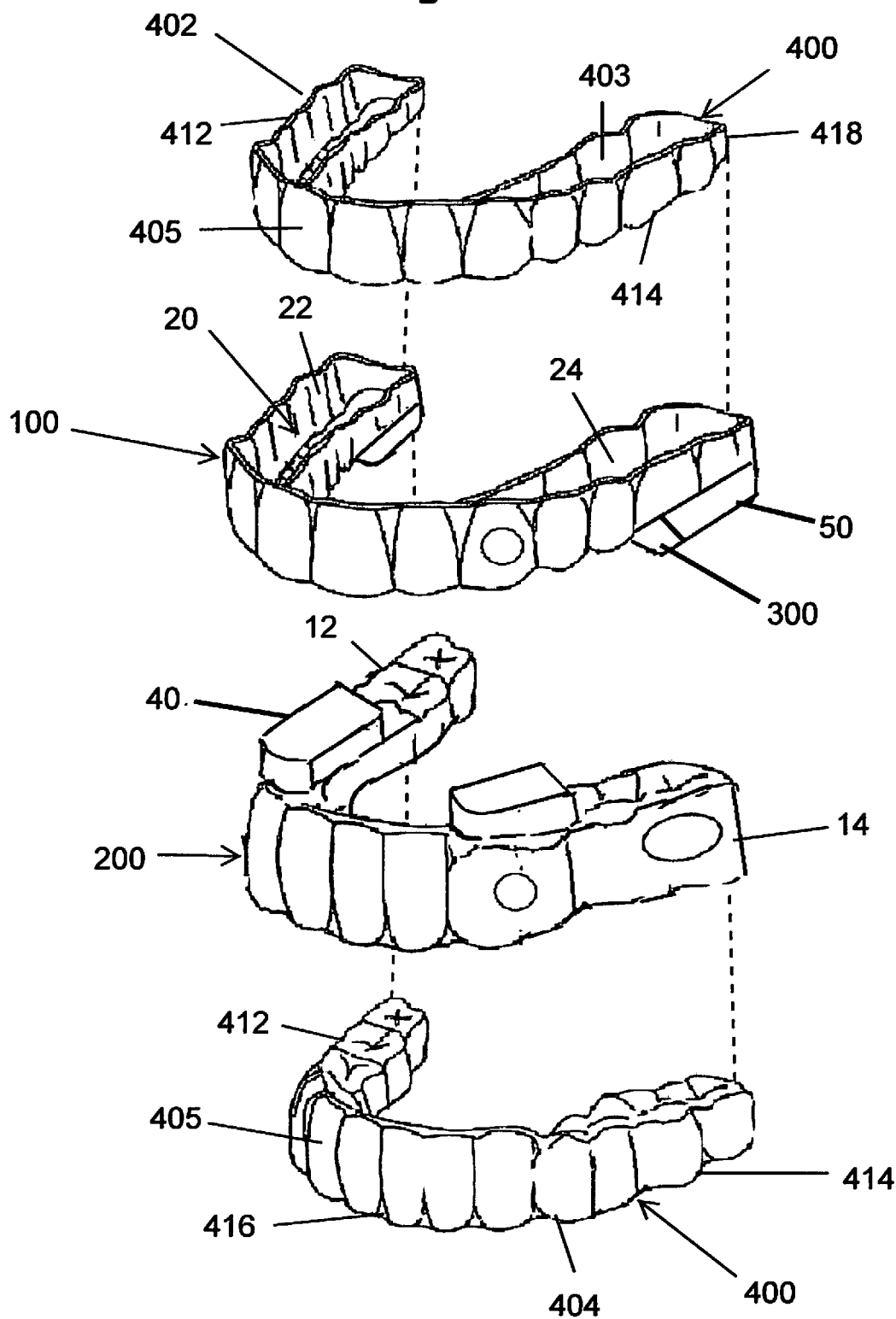
FIG. 14 is an exploded, top left side perspective view of an alternative embodiment of the present appliance for use with dental trays.

In another embodiment, shown in FIG. 14, the present trays 15 can be designed to be used in combination with a set of separately formed orthodontic trays 400, typically formed from a polymer material. As shown in FIG. 14, each of such orthodontic trays 400 usually comprises an upper orthodontic tray 402, a lower orthodontic tray 404, an inner surface 403 for contacting at least some of a subject's teeth, an outer surface 405, an anterior portion 416, a posterior portion 418, a right side 412, and a left side 414. In this embodiment, the receptacle 20 of the present appliance 10 is sized to receive and reversibly retain an orthodontic tray 400, generally by contacting an outer surface 405 of an orthodontic tray 400. In this way, a subject can use the orthodontic trays 400 during the day and then continue using them at night in combination with the present appliance 10 in order to obtain relief from sleep apnea.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. An oral appliance for treating snoring and/or sleep apnea in a subject, comprising:
   (1) an upper tray having an anterior portion, a posterior portion, a right side, a left side, a buccal side, a lingual side, an interior surface, and an outer surface, the upper tray comprising:
      (a) a receptacle bounded by the interior surface of the upper tray;
      (b) a right side upper bite pad connected at an upper end to a lower surface of the right side of the upper tray, wherein the right side upper bite pad comprises a lower surface, an anterior surface, a posterior surface, a right side, and a left side, the right side upper bite pad extending anteriorly from a posterior portion of the right side of the upper tray, wherein the lower surface of the right side upper bite pad is lower than the lower, coronal surface of an anterior portion of the right side upper tray;
      (c) a first right side insert comprising an upper surface, a lower surface, an anterior surface, a posterior surface, a right side, and a left side, wherein the upper surface faces and/or contacts the lower surface of the right side of the upper tray anteriorly with respect to the right side upper bite pad, and wherein the anterior surface of the right side upper bite pad comprises a recess and the posterior surface of the first right side insert comprises a projection adapted to fit within the recess and thereby secure the first right side insert to the right side upper bite pad;
      (d) a left side upper bite pad connected at an upper end to the lower surface of the left side of the upper tray, wherein the left side upper bite pad comprises a lower surface, an anterior surface, a posterior surface, a right side, and a left side, the left side upper bite pad extending anteriorly from a posterior portion of the left side of the upper tray, wherein the lower surface of the left side upper bite pad is lower than the lower, coronal surface of an anterior portion of the left side upper tray;
      (e) a first left side insert comprising an upper surface, a lower surface, an anterior surface, a posterior surface, a right side, and a left side, wherein the upper surface faces and/or contacts the lower surface of the left side of the upper tray anteriorly with respect to the left side upper bite pad, and wherein the anterior surface of the left side upper bite pad comprises a recess and the posterior surface of the first left side insert comprises a projection adapted to fit within the recess and thereby secure the first left side insert to the left side upper bite pad; and
      (f) a buccally facing anterior right side anchor on the outer buccal surface of the anterior portion of the right side of the upper tray, and a buccally facing anterior left side anchor on the outer buccal surface of the anterior portion of the left side of the upper tray; and
   (2) a lower tray having an anterior portion, a posterior portion, a right side, a left side, a buccal side, a lingual side, an interior surface, and an outer surface, the lower tray comprising:
      (a) a receptacle bounded by the interior surface of the upper tray;
      (b) a right side lower bite pad connected at a lower end to the upper surface of the right side of the lower tray, wherein the right side lower bite pad comprises an upper surface, an anterior surface, a posterior surface, a right side, and a left side, the right side lower bite pad extending posteriorly from an anterior portion of the right side of the lower tray, wherein the upper surface of the right side lower bite pad is higher than the upper, coronal surface of a posterior portion of the right side lower tray;
      (c) a left side lower bite pad connected at a lower end to the upper surface of the left side of the upper tray, wherein the left side lower bite pad comprises an upper surface, an anterior surface, a posterior surface, a right side, and a left side, the left side lower bite pad extending posteriorly from an anterior portion of the left side of the lower tray, wherein the upper surface of the left side lower bite pad is higher than the upper, coronal surface of a posterior portion of the left side lower tray;
      (d) a buccally facing anterior right side anchor on the outer buccal surface of the anterior portion of the right side of the lower tray, and a buccally facing anterior left side anchor on the outer buccal surface of the anterior portion of the left side of the lower tray; and
      (e) a buccally facing posterior right side anchor on the outer buccal surface of the posterior portion of the right side of the lower tray, and a buccally facing posterior left side anchor on the outer buccal surface of the posterior portion of the left side of the lower tray, wherein the anterior surface of the right side insert comprises an engagement surface which contacts the posterior surface of the right side lower bite pad, and wherein the anterior surface of the left side insert comprises an engagement surface which contacts the posterior surface of the left side lower bite pad, thereby limiting the forward positioning of the upper tray with respect to the lower tray, thereby alleviating snoring and/or apnea when the oral appliance is used by a subject; and wherein the receptacles of the upper tray and the lower tray are each configured to receive and retain an orthodontic tray, or wherein the receptacles of the upper tray and the lower tray are each configured to reposition one or more teeth of a subject and/or to change the configuration of a subject's mandible and/or maxilla when the appliance is worn by the subject.

2. The oral appliance of claim 1, further comprising an elastic band connecting the anterior left side anchors of the upper tray and the lower tray, an elastic band connecting the anterior right side anchors of the upper tray and the lower tray, an elastic band connecting the anterior left side anchor of the upper tray with the posterior left side anchor of the lower tray, and an elastic band connecting the anterior right side anchor of the upper tray with the posterior right side anchor of the lower tray.

3. The oral appliance of claim 1, wherein the anchors are selected from the group consisting of a button, a hook, and a Herbst screw.

4. The oral appliance of claim 1, wherein each insert is connected to a respective bite pad with an interference fit.

5. The oral appliance of claim 1, further comprising a second right side insert and a second left side insert provided with the appliance, wherein the second right side insert and second left side insert each have a pair of lateral sides, and wherein the length of the lateral sides of the second right side insert and second left side insert are different than the length of the first right side insert and first left side insert.

6. The oral appliance of claim 1, wherein the projections of the first right side insert and the first left side insert each comprises a wedge having sides that extend laterally and posteriorly and the recesses of the right side lower bite pad and the left side lower bite pad each is wedge-shaped and configured to receive and retain the respective projection.

7. The oral appliance of claim 1, further comprising a first orthodontic tray and a second orthodontic tray, wherein the orthodontic trays can be received within the receptacles of the oral appliance.

8. The oral appliance of claim 7, wherein the orthodontic trays comprise a series of first orthodontic trays and a series of second orthodontic trays, and wherein each of the orthodontic trays in the series comprises a different configuration in order to change the position of the subject's teeth and/or the shape of the subject's jaw.

9. The oral appliance of claim 8, wherein the receptacles of the upper tray are shaped to receive all of the first orthodontic trays, and the receptacles of the lower tray are shaped to receive all of the second orthodontic trays.

10. The oral appliance of claim 1, wherein the anchors of the first tray are mechanically connected to the anchors of the second tray with connectors selected from the group consisting of orthodontic rubber bands, telescoping shims, and plastic connectors.

11. A method of treating snoring and/or sleep apnea comprising the step of providing the oral appliance of claim 1 to a subject in need thereof.

* * * * *